(12) United States Patent
Gandini et al.

(10) Patent No.: US 8,556,843 B2
(45) Date of Patent: Oct. 15, 2013

(54) BLOOD PURIFICATION METHOD AND APPARATUS FOR THE TREATMENT OF MALARIA

(75) Inventors: Alberto Gandini, Pittsburgh, PA (US); Roy Weinstein, Houston, TX (US); Ravi-persad Sawh, Missouri City, TX (US); Drew Parks, Houston, TX (US)

(73) Assignee: AccelDx, Pittsburgh, PA (US)

( * ) Notice: Subject to any disclaimer, the term of this patent is extended or adjusted under 35 U.S.C. 154(b) by 99 days.

(21) Appl. No.: 12/865,411

(22) PCT Filed: Feb. 2, 2009

(86) PCT No.: PCT/US2009/000682
§ 371 (c)(1),
(2), (4) Date: Aug. 26, 2010

(87) PCT Pub. No.: WO2009/097159
PCT Pub. Date: Aug. 6, 2009

(65) Prior Publication Data
US 2010/0331753 A1    Dec. 30, 2010

Related U.S. Application Data

(60) Provisional application No. 61/271,647, filed on Feb. 2, 2008, provisional application No. 61/205,751, filed on Jan. 22, 2009.

(51) Int. Cl.
*A61M 37/00* (2006.01)
*B03C 1/00* (2006.01)

(52) U.S. Cl.
USPC ....... 604/6.01; 604/5.01; 604/5.02; 604/5.04; 209/213; 209/223.1; 209/231; 209/232

(58) Field of Classification Search
USPC ......... 604/4.01–6.16; 210/223, 695; 209/213, 209/223.1, 231, 232
See application file for complete search history.

(56) References Cited

U.S. PATENT DOCUMENTS 3,985,646 A * 10/1976 Oder ............................ 209/214
5,116,965 A    5/1992 Ravetch et al.
(Continued)

FOREIGN PATENT DOCUMENTS

| EP | 1306211 A2 | 5/2003 |
| WO | WO8901785 | 3/1989 |
| WO | WO92/12129 | 8/1992 |

*Primary Examiner* — Philip R Wiest
*Assistant Examiner* — Benjamin Klein
(74) *Attorney, Agent, or Firm* — Acker Wood IP Law, LLC; Gwen R. Acker Wood

(57) ABSTRACT

Methods for treating malaria are provided, the treatment comprising the step of removing malaria-infected red blood cells from the patient's blood. Blood is drawn from the patient's circulatory system and circulated through a blood purification device that selectively eliminates the infected red blood cells from all other blood's components and replaces the cleansed blood back into the patient's circulatory system. A blood purification device, which is useful to perform the therapeutic methods of the invention, is also provided. The device leverages the magnetic properties of the hemozoin contained within the infected red blood cells and comprises one or more separation chambers (4) though which blood flows through a high-gradient magnetic field generated by an array of wires (5) separated from the chambers and not in contact with the patient blood. The magnetic field gradient acting on the cells magnetic properties displaces the infected and non-infected red blood cells on different layers of the blood flow across the chamber height. The blood flow is split into separated streams and blood streams containing infected cells are filtrated thereby trapping infected cells. Blood containing non-infected red blood cells is circulated back to the patient. The device application is not limited to the treatment of malaria and includes other blood related diseases that affect the magnetic properties of a patient's red blood cells.

19 Claims, 6 Drawing Sheets

(56) References Cited

U.S. PATENT DOCUMENTS

| | | | |
|---|---|---|---|
| 5,130,416 | A | 7/1992 | Wellems et al. |
| 5,186,827 | A | 2/1993 | Liberti et al. |
| 5,200,084 | A | 4/1993 | Liberti et al. |
| 5,295,382 | A | 3/1994 | Wellems et al. |
| 5,393,523 | A | 2/1995 | Knapp et al. |
| 5,395,614 | A | 3/1995 | Knapp et al. |
| 5,465,849 | A | 11/1995 | Wada et al. |
| 5,466,574 | A | 11/1995 | Liberti et al. |
| 5,476,741 | A | 12/1995 | Maret et al. |
| 5,476,785 | A | 12/1995 | Wellems et al. |
| 5,604,117 | A | 2/1997 | Maret et al. |
| 5,663,051 | A | 9/1997 | Vlasselaer |
| 5,691,208 | A * | 11/1997 | Miltenyi et al. ............... 436/526 |
| 5,795,470 | A | 8/1998 | Wang et al. |
| 5,827,681 | A | 10/1998 | Krug et al. |
| 5,849,307 | A | 12/1998 | Metz et al. |
| 5,976,369 | A | 11/1999 | Howe et al. |
| 5,980,479 | A | 11/1999 | Kutushov |
| 5,985,153 | A | 11/1999 | Dolan et al. |
| 5,993,665 | A | 11/1999 | Terstappen et al. |
| 6,103,113 | A | 8/2000 | Saho et al. |
| 6,193,071 | B1 * | 2/2001 | Stelzer ....................... 209/223.1 |
| 6,616,623 | B1 * | 9/2003 | Kutushov ..................... 604/6.09 |
| 6,688,473 | B2 | 2/2004 | Franzreb et al. |
| 7,223,345 | B2 | 5/2007 | Franzreb et al. |
| 2002/0074266 | A1 * | 6/2002 | Franzreb et al. .............. 209/213 |

* cited by examiner

BLOOD PURIFICATION METHOD AND APPARATUS FOR THE TREATMENT OF MALARIA

This Application is a 371 of international application no. PCT/US09/00682, filed 2009 Feb. 2, expired, which claims priority to U.S. Provisional Patent Application No. 61/205,751, filed 2009 Jan. 22, expired, and U.S. Provisional Patent Application No. 61/271,647, filed 2008 Feb. 2, expired.

FIELD OF THE INVENTION

The invention described here relates to a novel therapeutic process for the treatment of conditions characterized by parasitized blood cells, such as malaria.

BACKGROUND OF THE INVENTION

The Malaria Parasite Lifecycle and the Disease Pathogenesis

Malaria continues to place an unacceptable burden on the health and economic development in over 100 countries. One to two million people die of malaria each year and most of them are children under the age of five. A child dies from malaria every 30 seconds, and 350 to 500 million malaria cases are estimated annually worldwide (World Malaria Report 2008, "WHO/HTM/GMP/2008.1", ISBN 978 92 4 156369 7).

Malaria is caused by the protozoan parasite of the genus *Plasmodium*. Four species of *Plasmodium* affect humans, and these are *P. falciparum, P. vivax, P. ovale*, and *P. malariae*. Of these, the *P. falciparum* is responsible for 90% of the world malaria mortality. In humans, the infection is initiated with the meal bite of an Anophilis mosquito injecting the sporozontes of the *Plasmodium* while feeding. After an initial incubation period in the human liver, the *Plasmodium* parasite undergoes an exoerythrocytic schizogony (i.e., an asexual replication), after which the merozoites (the daughters cells) enter the blood circulatory system and penetrate the red blood cells (RBCs) which become parasitized (pRBCs). In the pRBCs, the parasite grows by feeding off the hemoglobin; during this intra-RBC phase the parasite is known as a trophozoite. The early trophozoites are referred to as the ring form, due to their ring shape. In the late stage the trophozoites undergo a nuclear division, during which the parasite is known as a schizont. The trophozoites cycle terminates with schizonts undergoing an asexual replication, from which merozoites bud. Following the budding of the merozoites, the pRBC bursts, releasing into the blood stream these merozoites that quickly infect new RBCs. "Burst" is used herein to refer to the breakdown of the pRBC at the end of the parasite intra-erythrocyte lifecycle. The process continues cyclically with the number (percentage) of infected RBCs (parasitemia) growing rapidly and causing life-threatening consequences for the infected human. The intra-RBC cycle of the parasite varies between 24-72 hours, depending on the species, and the bursting of each pRBC releases several merozoites (Arrow et al., "Saving Life, Buying Time, Economics of Malaria Drugs in an Age of Resistance", *Institute of Medicine of the National Academies,* 2004).

Out of the many merozoites infecting the RBCs, few differentiate into a sexual form known as microgametocytes. These larger parasites fill up the erythrocyte and are ingested by mosquitoes during the human blood feeding. These gametocytes reproduce inside the mosquito from which sporozoites are born. These sporozoites, born within the mosquito, are then transferred on to other humans during subsequent bites. The infection cycle from mosquito to human and back to mosquito and human again is thus completed. In order to reproduce, the malaria parasite requires a mosquito and a human phase. The disease would continue to perpetuate until the reproduction cycle is interrupted. This interruption could be achieved by either preventing the mosquito's bites or by eliminating the microgametocytes. In fact, while these microgametocytes are not responsible for the pathogenesis of the disease, they are directly responsible for the disease transmission and a key element in the reproduction cycle of the parasite (Miller et al., *Nature* 415: 673-679, 2002). Without the mosquito ingesting the gametocytes present in the individual's infected blood, the parasite would not reproduce in the mosquito and the infection cycle would be interrupted.

The parasite blood stage is responsible for the pathology associated with malaria. If untreated, malaria rapidly results in a life-threatening disease. The most common side effects include fever, anemia, and respiratory distress. As the number (percentage) of pRBCs increase, the patient progressively sickens. When the fraction of pRBCs reaches about 5% of the total RBCs, strokes, coma, and multiple organ failures are among the potential complications and causes of death (World Malaria Report 2008, "WHO/HTM/GMP/2008.1", ISBN 978 92 4 156369 7 and Arrow et al., "Saving Life, Buying Time, Economics of Malaria Drugs in an Age of Resistance", *Institute of Medicine of the National Academies,* 2004). This stage of the disease is referred to as severe malaria and cerebral malaria if the brain is the organ most affected by the disease. These stages of the disease lead to a rapid death if untreated in most cases. However, even under the current treatment method, the mortality rate of severe malaria is exceptionally high.

The malaria pathogenesis is a very complex process affecting several organs and tissues, and as of today it is not yet fully understood (Miller et al., *Nature* 415: 673-679, 2002). The principle pathophysiological future of severe malaria is the metabolic acidosis, which leads to the commonly observed respiratory distress in severe malaria. There are several causes of acidosis: i) Liver failure; ii) increase in lactic acid stimulated by the immune system (cytokines) that is reacting to the release of the parasite toxic byproduct (hemozoin) following the RBCs' burst; iii) the reduction of oxygen delivery to several tissues—the absence of oxygen in tissue further stimulates the formation of acidosis. The reduction of the oxygen delivery is caused by the combination of several factors. First, an increasing anemia due to the destruction of RBCs by the parasite—every 48 hours the pRBCs burst and are removed from the total RBC's count. Second, the *P. falciparum* alters the RBC's surface protein, causing the RBCs to change shape, deformability, ability to adhere to the vessel surface, and a reduction of the deformability in non-infected RBCs. These factors increase blood viscosity, obstruct the flow of other RBCs, and thus ultimately compromise the blood flow. The changeover in blood rheology that follows this set of events is ultimately the cause of malaria-induced complications, including kidney failures and strokes. Current Malaria Treatments: Anti-Malarial Drugs and Exchange Transfusion.

At present, malaria is treated with one or more of numerous pharmaceutical drugs. A brief list of drugs includes chloroquine, sulfadoxine-pyrimethamine, mefloquine, atovaquone-proguanil, amodiaquine, quinine, doxycycline, and artemisin derivatives (Arrow et al., "Saving Life, Buying Time, Economics of Malaria Drugs in an Age of Resistance", *Institute of Medicine of the National Academies,* 2004; Griffith et al., *JAMA.* 297(20):2264-2277, 2007; Yakoub et al., "Handbook of Drugs for Tropical Parasitic Infections", Taylor & Francis Inc., 1995). In the last three decades, most malaria endemic regions have seen the growth of parasite strains that are immune to one or more drugs with only the exception of the artemisin compounds. However, the lack of artemisin resistance is believed to be due to the limited use of these compounds in endemic regions. In fact, the World Health Organization (WHO) fears that once the artemisin compounds are widely used, parasite strains would develop a resistance to the artemisin compounds and spread through the world endemic regions. If artemisin resistance were to develop, it would signal the end of anti-malarial drugs with severe consequence on the spread of the disease. The development of a parasite strain resistant to artemisin is highly probable. Research studies have shown that all drugs entered in the mass-market bore resistant parasite strains within ten years from their market introduction.

In addition to the growing parasite resistance, all anti-malarial drugs have other severe pitfalls and side effects. These drawbacks may include a low efficacy of a given anti-malarial that varies with the parasite strain or a considerable reduction in efficacy of a given anti-malarial regarding the progression of the disease into the severe stage. While a drug may effectively work in treating malaria in the early stage of the infection, its effectiveness is considerably lower in severe episodes. A further drawback to relying on anti-malarials is that a long term window for the drugs is often required before they become effective. Severe malaria strains may induce death within 24 hours, and since malaria infection often goes undetected and/or unrecognized, untreated malaria even in the early stage of the infection is a life threatening disease (World Malaria Report 2008, "WHO/HTM/GMP/2008.1", ISBN 978 92 4 156369 7; Arrow et al., "Saving Life, Buying Time, Economics of Malaria Drugs in an Age of Resistance", *Institute of Medicine of the National Academies*, 2004; Miller et al., *Nature* 415: 673-679, 2002; Griffith Kevin S. et al., *JAMA*. 297(20):2264-2277, 2007; Yakoub et al., "Handbook of Drugs for Tropical Parasitic Infections", Taylor & Francis Inc., 1995)

In conclusion, a set of factors that includes the ability of the malaria parasite to rapidly mutate and build resistance to drugs, the low efficacy of current drugs, combined with the mentioned side effects and shortcomings, indicate that a better solution is needed in order to treat malaria and reduce disease transmission.

Exchange Transfusion

Exchange transfusion is often considered the treatment of last resort for severe and cerebral malaria and it is the only non-drug based anti-malarial treatment currently available. Exchange transfusion is a medical technique used to replace the whole blood or one of its components, e.g., RBCs, of a patient with that of healthy donors. Exchange transfusion as a life-saving procedure has been applied to treat various blood-based diseases other than malaria, including neonatal polycythemia, Rh-induced hemolytic disease of the newborn, severe sickle cell crisis, and toxic effects of certain drugs.

Exchange transfusion (ET) as a treatment to malaria was first reported by Gyr et al. in 1974 (Gyr et al., *Schweiz Med Wochensch;* 104:1628-30, 1974). Since then, the benefits of ET have been reported in numerous research and clinical reports (Griffith Kevin S. et al., *JAMA*. 297(20):2264-2277, 2007; Hoontrakoon et al., *Tropical Medicine and Internal Health*, 3(2):156-161, 1998; White N J, *Journal of Infection* 39:185-186, 1999; Mordmuller et al., *Clinical Infectious Diseases* 26:850-2, 1998; Udani et al., IJCCM 7(2), 2003; Boctor F N, *Pediatrics* 116(4), 2005; Boctor et al., *Transfusion,* 43:549, 2003; Shanbag P et al., *Ann Trop Paediatr.* 26(3):199-204, 2006; Mehta et al., *J. Commun Dis.* 38(2):130-8, 2006; Powell et al., *Transfusion Medicine Reviews*, 16(3): 239-250, 2002). These studies have shown that exchange transfusion may reduce the morbidity rate and contribute to a faster recovery time.

For example, it has recently been reported that performing exchange transfusion on patients in the severe stage of the disease results in a significant health improvement and rapid reduction of parasitemia. One study, in which blood exchange transfusion was performed on a 23-year old patient with 43% parasitemia, cerebral involvement, fever, and jaundice. Following two exchange transfusion treatments the patient recovered, and the parasitemia level rapidly decreased to 0.01%. In another study (Powell et al., *Transfusion Medicine Reviews,* 16(3): 239-250, 2002) a sample of 27 patients affected by severe malaria were treated with blood exchange transfusion. The level of survival was 89%, and in 25% of the patients, a prompt neurological improvement was observed. Another study (Hoontrakoon et al., *Tropical Medicine and Internal Health,* 3(2):156-161, 1998) showed that ET was safe and well tolerated by the patients. It also showed a 20% reduction in mortality when ET was used in conjunction with drugs whereas the mortality rate of those patients that did not received ET was as high as 69%.

The effectiveness of the blood exchange transfusion and the rapid recovery of patients with severe malaria following exchange transfusion have been attributed to various factors (Feldman et al., "Tropical and Parasitic Infections in the Intensive Care Unit", Springer, 2004). First, by removing the infected RBCs from the circulation the parasite burden is lowered. Second, exchange transfusion also permits the rapid reduction of the antigen load, parasite-derived toxins, and parasite-produced metabolites and toxic mediators released in the blood when RBCs explode. Finally, exchange transfusion in malaria patients results in the replacement of rigid pRBCs and unparasitized RBCs with healthy RBCs that are more deformable, thereby alleviating microcirculatory obstruction.

ET is often considered a last resort method and scarcely performed for its numerous risks, high cost, labor-intensive procedure and lack of sufficient donors to provide safe blood. In fact, whereas the potential benefits of ET are significant, ET also has numerous side effects and substantial risks. Risks and complications include but are not limited to blood clots, changes in blood chemistry, heart and lung problems, infections, shocks due to inadequate blood replacement or blood overflow, and immunological rejection risk associated with injecting large volume of whole blood from several donors, each one with a different antibody system.

In addition to these risks, exchange transfusion is a difficult practice requiring significant medical expertise and is inherently impractical on a large scale because of the large amount of blood it requires. Each exchange transfusion requires up to several units of screened and healthy blood. Blood banks even in developed countries like the U.S. and Western Europe run below optimal quantity. In most of the regions affected by malaria, especially in the sub-Saharan regions, the population is also strained by several other infective diseases, poverty, a lack of specialized centers for blood collection and storage, and famine. It is highly unlikely to imagine that enough healthy blood could be collected to effectively solve the malaria problem on a significant scale. In addition, the World Health Organization (WHO) recognized that malaria contributes indirectly to HIV transmission through transfusions with infected blood to patients with severe malaria, and concluded that is not possible to make any general recommendation since the risks may outweigh the benefits associated with exchanging blood between donor and patient. Unable to give direct guidelines, the WHO leaves to the discretion of individual doctors the decision to perform the blood exchange transfusion as the last life-saving resource available.

These factors contribute ultimately to the reasons for the limited use of ET, and help explain why ET is performed only in those extremely severe episodes that manage to reach well-equipped hospitals where the supply of screened blood is readily available, and cost and labor issues are less significant.

Furthermore, although ET has been performed numerous times in numerous hospitals, a comprehensive clinical trial proving the benefits of ET with a statistically significant margin has not yet been completed. However, the lack of extensive study is to be attributed to the underlying awareness in the medical community that even if ET were to be effective, it would not be a mass-applicable technique because of the costs and prohibitive requirements for fresh blood.

Nevertheless, despite the lack of comprehensive clinical trials, the numerous medical reports and research papers provide evidence of the beneficial effects of ET in malaria treatment. Many experts encourage ET as an adjunct treatment for patients with a parasitemia level greater than 10% and for which drug treatment is failing.

Blood Apheresis Technology and its Limitations

The procedures and devices used in an ET may vary depending on the blood composition that is being transfused. In treating malaria, ET may be performed manually or automatically using various apheresis systems. Manual ET is typically performed by withdrawing the patient's blood in small amounts of about 100 ml through a venous catheter. An equal amount of donor's blood is then injected through a secondary blood vessel, which is often placed in the other arm. The cycle is repeated until the correct volume of blood has been replaced, and the level of parasitemia reduced, by either replacing the entire patient's blood volume or a fraction of it, which varies case by case. Typically during an ET process, several blood volumes are transferred from donors to patient (1 unit of blood volume is typically 500 ml).

In automatic ET processes, clinicians may use various apheresis systems (Bruce et al., "Apheresis: Principles and Practice", American Association of Blood Banks (AABB), 2003). For example, a patient may be attached to a plasmapheresis or erythropheresis machine that continuously withdraws blood and separates the plasma from the RBCs by centrifugation. In a plasmapheresis, the plasma is enriched with healthy RBCs and circulated back to patient's circulatory systems; in an erythropheresis, the RBCs are added to frozen plasma and injected back into the patient's circulatory systems. An example of the use of these devices is found in Boctor et al. (Boctor F N., *Pediatrics*, 116(4, 2005), in which the author reported using the COBE spectra apheresis system (COBE Laboratories, Lakewood, Colo.) to remove the patient's RBCs and replace them with donor RBCs.

Despite few technical differences, all current devices using ET achieve separation by centrifugation technology leveraging the density difference between the various blood components.

Magnetic Property of Malaria Parasitized Red Blood Cells

Malaria infected RBCs have magnetic properties that differ significantly from those of healthy RBCs and all other blood's cells (Hackett et al., *Biochimica et Biophysica Acta*, 1792: 93-99, 2009; Sullivan et al., "Biopolymers, Volume 9", Wiley-VCH Verlag GmbH & Co, P., 2002; Moore et al., *FASEB J.* 2006 April; 20(6):747-9. *Epub* 2006 Feb. 6.). After penetrating the RBCs, the parasite converts the heme groups into an insoluble highly compacted crystal known as "hemozoin". The conversion is made by the parasite to detoxify the heme. The hemozoin is present in all intra-erythrocyte stages of the parasite—the ring, trophozoite, schinzont, and gametocyte stages—and it occurs in all *Plasmodium falciparum* species. When the parasite reaches maturity and the RBC bursts, the hemozoin is released in the blood and scavenged by white blood cells.

Each heme-group contains a high-spin $Fe^{+3}$ (S=5/2) stacked in close proximity. The Fe—Fe atomic separation is around 8 angstrom (Andrzej et al., *J. Am. Chem. Soc.* 128: 4534-4535, 2006). The transformation of low-spin ($Fe^{+2}$) diamagnetic oxyhemoglobin into high-spin (Fe+3) hemozoin and the close proximity of the Fe atoms give rise to the strong paramagnetic properties of the hemozoin. Studies have shown that the amount of heme converted into hemozoin increases linearly during the parasite intra-erythrocyte lifecycle. It has been estimated that prior to the RBC bursting, nearly 80% of the hemoglobin was consumed and its heme converted to hemozoin.

Hemozoin has been used in various ways—to develop vaccine and drug treatments, diagnostic modality, and for a magnet-based technology to enrich pRBCs. The following is a list of representative patents related to the use of hemozoin: U.S. Pat. Nos. 5,116,965; 5,130,416; 5,296,382; 5,393,523; 5,395,614; 5,476,785; 5,478,741; 5,604,117; 5,827,681; 5,849,307; see also WO89/01785; and WO92/12129.

Because the hemozoin is contained in the parasite vacuole, the parasite itself, and the pRBCs are also paramagnetic. Experimental studies show that pRBCs increase their magnetic susceptibility as they age, because of the increased amount of hemozoin produced by the parasite (Hackett et al., *Biochimica et Biophysica Acta*, 1792: 93-99, 2009; Moore et al., *The FASEB Journal Express Article* doi:10.1096/fj.05-5122fje, Published online Feb. 6, 20066). These studies showed that in the late stages, the pRBCs had magnetic susceptibility of between $1\text{-}2\times10^{-6}$ in (SI) unit, which is larger by a factor of about 10-fold than the magnetic susceptibility of un-parasitized oxygenated RBCs and of all other blood cells and plasma. For example, oxygenated un-parasitized RBCs have magnetic susceptibility around $-0.2\times10^{-6}$ in (SI) unit (Coryell et al., *Proc. Natl. Acad. Sci. U.S.A.* 22(4): 210-216, 1936; Taylor D S, *J. Am. Chem. Soc.*, 60(5), pp 1177-1181, 1938). In these studies magnetic susceptibility is often reported with respect to water, since plasma has magnetic susceptibility very close in magnitude to the water's susceptibility. The magnetic property of the pRBCs has been exploited using a magnetic separator, of the type described in next section, as a technique to enrich pRBCs for routine culture and analysis. For example, early researchers have used magnetic field gradients to remove pRBCs from small blood samples of about 10 ml or less (Paul et al., *The Lancet*, 318(8237):70-71, 1981). Others have used the magnetic properties to design diagnostic tests. Recently, isolation of malaria pRBCs using commercial high-gradient magnetic separators (MACS technology, Miltenyi Biotec GmbM, Gladbach, Germany) has been performed with levels of separation efficacy close to 95% (Uhlemann et al., *Macs&more*, 4(2), 2000). These separators are substantially equivalent to the apparatus described in U.S. Pat. Nos. 3,567,026, 3,676, 337 and 3,902,994.

Magnetic Cell Separation Technology and its Limitations

A variety of bioparticle isolation and magnetic separation devices are known; see e.g., U.S. Pat. No. 6,361,749. In this section we address limitations of certain of these prior art devices and methods. Separation of pRBCs has been achieved using high-gradient magnetic separation of the type described, e.g., in U.S. Pat. Nos. 3,567,026, 3,676,337, 3,902, 994 and 5,691,208. In each such apparatus, a magnetic (steel) wool is placed into the separation chamber directly in contact with the test medium containing the target cells. Target cells that can be separated by this method are typically classified in two categories. The first includes cells that are either permanently magnetized or that have strong paramagnetic or ferromagnetic properties. The second category comprises cells that have very small magnetic properties but can be bound to magnetic beads coated with antibodies which bound specifically to the target cells. The separation chamber is then placed in a magnetic field created by permanent magnets, superconducting magnets, or electromagnets. The function of the steel or iron wool is to create a high magnetic field gradient, which generates a magnetic force on the magnetic particles within the medium, attracting and retaining the magnetic particles. In the typical operation method, the medium is placed into the separation chamber and under the force of gravity it percolates through the steel wool. While percolating, the magnetic labeled cells are retained by the iron or steel wool and in this process the medium is purified. Retention of targeted cells by magnetized steel or iron wool is one of the distinguishing characteristics of these devices. The use of gravitational force as the propulsive method is a second distinguishing characteristic of these apparatus.

The commercially available device MACS (Miltenyi Biotec GmbM, Gladbach, Germany) may be used as a bench top apparatus in routine analysis for research, but is not suited for separating large volumes of blood or for high concentrations of pRBCs. For example, a typical device of this kind with a steel or iron wool matrix of 13 cm3 separates pRBCs from whole blood at a rate of 2 ml/min. Therefore, to purify the average amount of blood in an adult (i.e., about 5-6 liters) using such devices would take over 50 hours of processing time. Furthermore, such devices are subject to clogging when the density of cells to separate is large. Typically a steel or iron wool filter of 40 ml in volume may trap about $1.3*10^{10}$ RBCs, after which the device clogs. In the blood of an adult patient with a parasitemia, e.g., of 20% and hematocrit of 40% (typical values for severe malaria) there are about $5*10^{12}$ pRBCs. Thus, a device using steel wool as a separating mechanism would require a filter with a volume as large as 16 liters.

There are other classes of devices that use a high magnetic field gradient to generate attractive forces and separate magnetic cells from non-magnetic mediums. See, e.g., U.S. Pat. Nos. 4,663,029, 5,465,849 and 6,688,473. Here, magnetic cells or particles in fluid are enclosed in a chamber and are separated by deviating the particle trajectory accordingly to their magnetic susceptibility. For example, in U.S. Pat. No. 4,663,029, a separator comprising a non-magnetic canister with a single magnetized wire extending parallel to the canister is described. This configuration limits the canister's height to about twice the wire's radius, and the canister's width to the wire diameter. Therefore, the cross section in this apparatus is limited to an area of about $4a^2$. For small cells like pRBCs with a susceptibility of about $1-2\times10^{-6}$ in (SI) unit, in a blood medium, to generate forces comparable in magnitude to the typical viscosity force the cells experience in the chamber (~10-100 pN), a wire must have radius a ranging between 10-100 µm. An apparatus of the type described in U.S. Pat. No. 4,663,029 applied to the separation of pRBCs would thus require a cross section of about $4\times10^{-8}$ meter$^2$, which at a fluid velocity of about ½ meter/sec would result in a flow rate lower than $2\times10^{-8}$ meter$^3$/sec. At this rate, more than 80 hours of processing time would be required to treat 5-6 liters of blood. And, while an apparatus of the type described in U.S. Pat. No. 5,465,849 applied to the separation of pRBCs might remove pRBCs from a patient, such an apparatus would also likely remove large amounts of the medium that surrounds the pRBCs (i.e., blood). As a result, an already weakened patient would be deprived of a portion of their healthy blood components. Moreover, after using an apparatus as described in U.S. Pat. No. 5,465,849, a large volume of blood and biohazard material would be remain as a waste product after the apparatus was used. This large volume of blood would then need to be safely disposed, thereby resulting in higher safety risks and processing costs.

Current magnetic cell separation technology is not applicable to a dialysis-like process where the patient's blood must be processed in short time, in continuous mode, and the pRBCs separated from the healthy RBCs and extracted from the patient blood circulatory system. For this and other reasons, it would be useful to have new and improved devices and methods for separating magnetically reactive materials from blood. Such devices and methods will be useful for treating patients with conditions characterized at least in part by infected or otherwise abnormal blood cells having magnetic properties that differ from normal or uninfected blood cells in the patient.

SUMMARY AND DESCRIPTION OF THE INVENTION

One objective of the invention is to provide an improved treatment for malaria which overcomes certain of the failures and/or side effects of current treatments. The present invention provides a novel process and a multi-stage blood purification apparatus for treating parasites of the blood, e.g., malaria, by selectively removing from the circulatory system of a patient parasitized red blood cells ("pRBCs"). The treatment comprises the step of selectively removing from the patient's blood pRBCs, and in the case of malaria, selectively removing hemozoin (which is a parasite by-product and a potent toxin), and free-heme released in the blood after the pRBCs burst. This malaria treatment is referred to herein as "malaria-apheresis".

The invention also provides a high-gradient laminar flow multi-stage blood purification device which is useful to perform the therapeutic methods of the invention. This device removes the pRBCs in a dialysis-like process, where the patient's blood is drawn and returned to the peripheral system through a draw and return line. The device operates by leveraging the intrinsic magnetic properties of the pRBCs, the blood viscosity, and the changes of blood viscosity associated with increasing levels of parasitemia. This device is designed to perform the therapeutic treatment methods of the invention for malaria and more generally, for removal from blood of any magnetically responsive agents or components.

A pRBC, as defined herein, refers to any parasite-infected (e.g., malaria-infected) RBC, regardless of the parasite species, strain or parasite lifecycle stage within the cell. For malaria, this includes the ring, trophozoite, schinzont and gametocyte lifecycle stages. During all of these stages, the parasite is producing hemozoin and thus makes the infected RBCs magnetic.

In certain embodiments, the invention provides a treatment for a patient diagnosed with malaria, the treatment comprising a process, malaria-apheresis, characterized by the safe removal (i.e., depletion or elimination) of some or substantially all of the pRBCs from a patient's circulatory system with minimal discomfort for the patient. In certain embodiments, the present malaria-apheresis process is applicable to malaria-infected patients with any level of parasitemia, whether the infection is from a single parasite species or from multiple species. It is expected to be most beneficial to patients with parasitemia above 5%. However, this treatment is also expected to be beneficial to those patients with parasitemia below 5%.

Other applications of the present methods and devices of the invention are envisioned in addition to the separation of pRBCs from whole blood. It is envisioned that methods and devices of the invention may be more broadly used in removing from blood any magnetically responsive/reactive agent, such as infected or diseased blood cells or other magnetically responsive/reactive blood components (e.g., carrier proteins and the like.) All blood-born diseases which result in a different shape, or hemoglobin structure of concentration would be treatable with the present process provided that these abnormal RBCs could be readily separated from whole blood. Because any changes in shape or hemoglobin structure ultimately affect either the magnetic properties of the abnormal cell with respect to other healthy cells, or the viscosity of the blood, the present apparatus may be useful in other blood purification processes similar to the one herein described.

Possible genetic diseases that may be treated by the methods and devices of the invention include, but are not limited to, hemochromatosis or sickle cell anemia. Sickle cell anemia can be treated with ET, but because there are currently no methods to separate the sickle cells from the normal RBCs, a large amount of blood must be used during the ET. This is a problem that would be reduced or alleviated using the methods and devices of the present invention.

The pRBCs and the interaction of the immune system with the parasite's toxic by-products are directly related to the malaria pathogenesis as described above. By eliminating these patient's cells, the malaria pathogen is removed and a faster recovery of the patient and a rapid reduction of the disease's debilitating side effects are expected.

The invention provides a device (interchangeably referred to herein as an apparatus) which may be used to facilitate malaria-apheresis and other magnetic based blood separation methods of the invention. The apparatus is designed to extract blood from the circulatory system of a parasite infected patient, e.g., a malaria patient; to selectively remove the pRBCs and the parasite toxic by-products such as hemozoin and free-heme from the blood; and to return the cleansed blood to the patient. The invention also provides a blood purification apparatus i) to remove the pRBCs from infected blood without exposing it to open air; ii) to achieve a high separation efficiency and resolution; iii) to provide a fast high volume blood purification device that does not damage the structure of the healthy RBC; iv) to remove the pRBCs without the stringent need of using blood donors; v) to allow the treatment of multiple patients; vi) and to provide a portable and low power consumption apparatus.

The novel blood apheresis device and associated methods of the invention (e.g., for treating parasite infections and purifying blood) leverage: i) the intrinsic magnetic properties of the various blood components including the pRBC magnetic properties; ii) the difference between these properties; iii) and the blood viscosity. These characteristics significantly distinguish the present invention from all other current blood apheresis devices used during ET treatment, which on the contrary, leverage the density differences between the RBCs and other blood components, and are not selective with respect to pRBCs and un-parasitized RBCs.

With respect to treating malaria, for example, the devices and methods of the invention leverage the magnetic properties of the hemozoin and of the pRBCs, and the difference between the pRBCs magnetic properties and all other blood components such as oxygenated RBCs, de-oxygenated RBCs, leukocytes and plasma. The invention also leverages the changes in blood viscosity due to the increasing surface rigidity of the pRBCs and of the un-parasitized RBCs.

In certain embodiments, the invention provides a novel high magnetic gradient laminar-flow magnetic separator that eliminates blood clogging, maximizes the magnetic force, and increases the blood flow rate. In certain embodiments, the apparatus operates by exploiting the magnetic properties of the hemozoin and of the infected RBC's, the laminar-flow of the blood between two plates, and a set of parallel high-gradient magnetic field generators comprising embedded steel wires. The parallel high-gradient magnetic field generators are positioned such that the magnetic gradient is periodic along the longitudinal direction of the separation chambers, but uniform across the separation chamber width.

In certain embodiments, an apparatus of the invention filters out parasitized or mutant RBCs from a patient's blood. Alternatively, the apparatus may also serve to filter other blood components, including, but not limited to, platelets, neutrophils, eosinophils, basophils, lymphocytes, monocytes, macrophages and dendritic cells. In addition, the invention may be used to filter pathogenic or foreign cells from a patient's bloodstream. Examples of foreign cells include bacteria, including but not limited to *E. coli, Listeria monocytogenes, Neisseria meningitidis, Streptococcus pneumoniae, Salmonella*, Group B *streptococcus*. "Foreign cells" are also intended to include cells of the patient infected by a virus, including but not limited to *Haemophilus influenzae* type b, HIV, HBV, HCV, West Nile Virus, ebola virus RNA viruses of the Arenaviridae, Filoviridae, Bunyaviridae, Togaviridae, and Flaviviridae families. In another embodiment, the devices and methods of the invention may be used to filter out excess toxins or excessive metals from a patient's bloodstream, such as in the case of iron overload.

In certain embodiments, the blood cells or pathogens to be removed by the invention are targeted based on their inherent magnetic properties. An example of this is the removal of pRBCs from the blood based on the inherent magnetic properties associated with these cells. In another embodiment, blood cells or pathogens are magnetically modified before they are removed from the blood. Such magnetic modifiers may include, but are not limited to, magnetic nanoparticles, magnetically labeled antibodies, or other such magnetically tagged labels.

In any of the embodiments of the invention, blood may be drawn in a continuous mode or in cycle mode. A combination treatment wherein a patient is treated at separate times with a continuous mode and a cyclic mode may also be performed. In a continuous mode, blood may be withdrawn from a patient, processed and then returned to the patient in a relatively continuous, uninterrupted manner throughout the duration of the treatment. In a cycle mode, a fraction of the blood is withdrawn, processed and then returned to the patient, preferably but not necessarily before a second blood fraction is drawn again. Accordingly, drawing blood, or the withdrawal of blood, is defined in the application as the removal of blood from a patient in either a continuous or cycle mode.

The duration of each treatment is expected to vary between individuals, depending on the initial level of parasitemia, the patient's health condition at the time of treatment, and patient's medical history. In addition, blood may be drawn at various rates compatible with the physical condition of the patient and the stage and parasitemia level of the disease. In certain embodiments, the process lasts until either all pRBCs are completely removed from the patient, until the level of parasitemia is reduced to a level below which drug treatment alone would be effective, or until the patient is expected to self-heal. Individuals respond differently to malaria, and the present invention accounts for these differences. A patient with low parasitemia between 0% and 5% and who is in relatively good physical condition may tolerate blood being drawn rapidly at a rate between 1-10 liters/hour. This would result in treatment duration between 1 and 6 hours. On the other hand, an adult patient or a child in critical condition and/or with a high level of parasitemia (ranges anywhere above 5%), may not tolerate blood being withdrawn rapidly. In these cases, there are two preferred embodiments: i) The blood flow rate drawn from the patient is reduced to a level that each specific patient can tolerate, while the duration of the treatment is extended. This procedure would limit the discomfort or risk for the patient while allowing for a constant reduction of parasitemia. In this case, the treatment duration is expected to range from a few hours to the length of the parasite reproduction cycle (which varies between species from 48-72 hours); ii) The present malaria-apheresis process is performed in cyclic steps. First, the patient's parasitemia is reduced rapidly, by processing blood at a fast rate but for a limited time. Then, the patient is left to rest and recover after which a second or multiple treatments is/are applied. This embodiment is preferred for patients for which any delay in reducing the level of parasitemia may result in a rapid death in less than 24 hours.

Blood may be removed by any adequate (varying from patient to patient) blood vessels (veins or arteries). Likewise, blood may be inserted back into the patient's circulatory system through the same vessel or any other adequate vessel (veins or arteries), as determined by the skilled practitioner.

In certain embodiments, the patient's blood is drawn from a patient blood vessel, and run through a magnetic separator chamber in which the pRBCs, the hemozoin, and the gametocytes are separated from other blood components. The cleansed blood is then returned to the patient's blood circulatory system as shown in FIG. 1. The pRBCs, the hemozoin, and the gametocytes are then removed from the apparatus and safely disposed. The process may remove all three components simultaneously or only one of them at a time.

Blood may be removed at a volumetric flow rate adequate for the health of the patient and the level of parasitemia. In certain embodiment, the flow rate of blood in the invention is between 0.1-10 L/hr. In another embodiment, the flow rate of blood in the invention is between 1-10 L/hr. In another embodiment, the flow rate of blood in the invention is between 3-10 L/hr. In yet another embodiment, the flow rate is between 5-10 L/hr. In a preferred embodiment, the flow rate of blood in the invention is greater than $2\times10^{-8}$ meter$^3$/second.

In certain other embodiments, the invention may be used in combination with a drug therapy. Drugs suitable for such a combinational therapy may include any of the anti-malarial compounds described in the Background section of this application as well as any other anti-malarial, anti-parasitic, antibiotic, anti-fungal, analgesic, anti-inflammatory or other desired drug treatment. For example, ET has been successfully applied in combination with intravenous quinine, and in combination with oral quinine and doxycycline. The invention may also be used in combination with a drug therapy used to treat other diseases/disorders. In addition, drugs that are known to have blood-thinning properties, i.e., aspirin or anti-inflammatory compounds, may also be used in combination with the invention in order to reduce the blood viscosity described above. In another embodiment, the invention may be supplemented by the addition of a healthy donor's blood.

The tubing used to transport blood may be made from any biocompatible material, such as the plastic polyvinyl chloride. Alternatively, the tubing may be made from one or more of a variety of other materials, including but not limited to, polystyrene, Polyethylene, Nylon 66, 11, 12, Urethanes, Polypropylene, Polycarbonate and ABS. In certain embodiments, the tubing is used in the invention immediately after it has been removed from its packaging. In another embodiment, the tubing is primed by flushing the tubing with an appropriate solution such as saline solution or blood. In certain embodiments, the tubing is removable and disposable.

In certain embodiments, the magnets used in the invention are permanent magnets, such as, for example, SmCo and NeFeB magnets. Alternatively, other possible magnets that may be used include, but are not limited to, ceramic magnets (Strontium and Barium Ferrite), flexible magnets neodymium magnets (Nd—Fe—B), samarium magnets and alnico magnets. The permanent magnets may also be substituted with a variety of electromagnetic sources. Electromagnets may be made from materials that include, but are not limited to, copper and superconductive material. In certain embodiments, the magnetic field is applied using an array of magnets. Alternatively, the magnetic field may be applied using a single magnet. Preferably, the magnetic field generated from the use of such magnet ranges from between 0.1-1.0 Tesla and is selected by the skilled artisan based on one or more criteria, such as, for example, the differential magnetic properties of blood components to be separated and viscosity of the blood or blood derived fluid in which those components are located.

In certain embodiments, the magnetic field is applied uniformly along the length or width of the separator chamber. Alternatively, the magnetic field is applied in a graded manner. One or more wires may be used, parallel or perpendicular to the length of the separation chamber, to create a desired magnetic field, as will be appreciated by one of skill in the art. In certain embodiments, the magnets are removable and replaceable. In certain embodiments, the wires are set parallel to the chamber's width. In these embodiments, as the cells pass through the chamber, they are pulled, independently of their vertical position, towards the magnetized wires, where the magnetic force is the strongest. Thus, in this configuration all cells as they move along the chamber are receiving strong magnetic force impulses that deviate their trajectory according to their magnetic properties.

In certain embodiments, a single magnetized wire is employed. In an alternative embodiment, a series of magnetized wires were utilized. In preferred embodiments, the wires that create the magnetic field gradient are not in contact with the medium, in this case the blood. In one embodiment, the magnetized wires are made of iron. Alternatively, the magnetized wires may be made of any magnetic materials with high susceptibility. Examples of other suitable magnetic materials include, but are not limited to, steel, nickel, cobalt and gadolinium as well as various magnetic composites such as magnetic polymers. The magnetized wires may but need not be round. Other shapes, such as oval or trapezoidal may also be utilized when designing the wires. In one embodiment, the magnetized wires will be placed 10-400 μm apart from each other. In one embodiment, the radius of the magnetized wires should range from about 5-100 μm, and in certain embodiments, should be of the order of about 30 μm. In certain embodiments, the magnetized wires are removable and replaceable. In certain embodiments, one wire array is employed for multiple chambers, such as for example, for every two chambers. One of the advantages of this design is that it minimizes the number of wires for chamber volume. This is important because it minimizes the overall volume of the device and also the material cost. The wire array creates a field gradient that acts on the cells flowing in the chambers located above and below the array. If one computes the total volume of these wires, and the volume of the chamber which is related to the wire radius (assuming a chamber height that is about 4-times the radius), the ratio between the chamber's volume and the wire's volume is about 1:5. If the chamber is made higher, this ratio would decrease to, e.g., about 1:6. If the chamber is made shorter, this ratio would increase to, e.g., about 1:4.

In certain embodiments, the magnetized wires pull the pRBCs, or other blood component of interest, towards the periphery of the separation chamber, while the other blood components are expected to flow down the center of the separation chamber. In another embodiment, the magnetic field is reversed, and the pRBCs, or other blood component of interest, are pushed towards the center of the separation chamber.

In certain embodiments, only a single separation chamber is used. In other embodiments, multiple separation chambers may be employed. In these cases, the multiple separation chambers may be arranged parallel to each other from top to bottom and/or side to side. This unique configuration achieves the following goals: i) it allows for a shortening of the device length, while processing the same blood volume per unit of time; ii) it allows for use of smaller permanent magnets and thus reduces cost; iii) the size of the magnetic gradient generator is reduced by a factor of two.

The separation chamber may be made of any biocompatible material, including but not limited to PVC, polystyrene, Polyethylene, Nylon 66, 11, 12, Urethanes, Polypropylene, Polycarbonate and ABS. The proper length of the separation chamber is related to the radius of the wire and the blood flow rate that may be needed. For a typical foreseen application, with blood flowing at a rate of about 6 liters/hour, the apparatus length may range between a few cm to 1-2 meters. In certain embodiments, the separator width is between 2-500 cm. In certain embodiments, the separator height is between 40-400 µm.

In certain embodiments, the separation chamber is a disposable attachment. In one such embodiment, the separation chamber is attached to the magnetic gradient generator. By making the chamber and magnetic gradient generator a single piece, the two parts can be easily removed together from the device chassis. In other embodiments, the magnetic gradient generators fix to the device chassis, and the separation chamber or chambers slide in between the magnetic gradient generators. By allowing the separation chamber to be removed as a separate unit, the chamber becomes the only component of the device that comes in contact with the patient's blood. The chamber may be made of any biocompatible material already known and used in dialysis.

In certain embodiments in which the separation chamber of the device is small enough, the patient's own blood pressure may be used to propel blood through the separation chamber. In other embodiments, blood is propelled and, optionally, blood flow and pressure is regulated, through use of a powered pump, optionally with one or more gauges. The power source for the pump may be a standard outlet or a battery. Possible battery types include, but are not limited to, carbon zinc, zinc-manganese dioxide, Zn/MnO2, alkaline, lithium, lithium ion, lead acid, gel cells, nickel-cadmium and nickel-metal hydride. Alternatively, the power source may be solar, geothermal, or compressed gas. Power sources may be combined with or backed up by other power sources. For example, the invention may rely on the sun as a primary power source but on a generator or battery as a back-up power source.

In certain preferred embodiments, the flow of blood in the invention is not reliant on solely gravitational forces. In certain embodiments, two pumps are used in the apparatus of the invention. However, the number of pumps may be increased or decreased appropriately in order to create the appropriate pressure needed to withdraw blood at a reasonable rate and with minimal discomfort to the patient. In certain embodiments, the pumps are removable and replaceable. As an alternative to drawing blood by pumps, blood may also be drawn directly using the patient's blood pressure.

In certain embodiments, the pump pressure is graded throughout the apparatus. In one embodiment, pRBCs, after having been pulled to the periphery of the chamber by the magnetic force, are extracted from the blood by means of a pressure gradient. This embodiment does not require a variation of the suspension's flow velocity along the chamber height, and it allows a continuous mode separation. While the pump pressure may differ, this difference may be by only a few PSI. On the other hand, depending on the desired processing rate, the difference between the different pump pressures may be as large as 1 to 10 PSI per cm of chamber length.

In certain embodiments, one or multiple gauges are incorporated in the apparatus of the invention in order to monitor the blood pressures associated with the various stages in the process. The gauges would preferably be located near one of the pumps found in the device, in order to appropriately monitor the pumping activity. Alternatively, gauges may be used to monitor the pressure of blood in the device associated with a patient's blood flow.

One or multiple outlets are positioned along the separation chamber, and magnetically responsive blood components, such as the pRBCs, or other blood components of interest, are diverted towards these outlets when a magnetic field is applied across the separation chamber. The magnetically responsive components concentrate towards these outlets rather than towards the one or more outlets (exit ports) through which the other blood components flow, thereby removing magnetically responsive components from the patient's blood. In certain embodiments, the size of the outlet's cross-section is uniform. Alternatively, the outlet cross-section may be graded. The width of the outlets may vary depending of the density of pRBCs present in the blood that is been processed, and it may vary between $\frac{1}{10}$ and 4 times the wire's radius. In certain embodiments, the outlets are removable and replaceable.

In certain embodiments, the pRBCs, or other blood component to be removed, are diverted to a filter that selectively removes the component of interest. Alternatively, no filter is present. In cases where no filter is present, the diverted pRBC-containing blood could either be discarded safely or directed into another tube, or series of tubes, in which the pRBCs are selectively removed.

In certain embodiments, one or more membranes act as filters which are used to capture magnetically responsive components in the blood that are diverted from the separation chamber through one or more outlets. A multitude of suitable membranes or filters are available in the art. In certain embodiments, the filtered plasma, absent the component of interest, e.g., hemozoin and pRBCs, is then directed back to reconnect with the blood carrying the unparasitized RBCs. This filter may be present in a suitable collection container, such as a bag, or alternatively, the filter is present within the tubing itself. In certain embodiments, the desired pore size of the membrane is limited on the upper side, and should be smaller than the size of the hemozoin crystal, which is 1-3 µm, and of the pRBCs' average size, which is between 2-8 µm. In certain preferred embodiments, the filter used in the device of the invention is a non-magnetized filter. In certain embodiments, the filter is removable and replaceable.

Discussion

The present invention uniquely differs from and offers significant advantages over current anti-malarial treatment. Current drugs, with no exception, target the biological properties of the malaria parasite. The complexity of the malaria parasite with its multiple forms, ability to mutate and fast reproduction cycle has defeated pharmaceutical research for over a century. The methods of the invention, in contrast, target not the parasite's biological properties but the unique physical properties of the infected RBCs. In particular, the invention leverages the magnetic properties and the rigidity of the infected RBCs.

Furthermore, the methods of the invention, while inspired by conventional ET, also differ significantly from ET in several aspects. Malaria-apheresis does not require blood donors, hence avoiding shortages of donated blood and eliminating the risk of transmitting diseases between donors and patients. Malaria-apheresis also eliminates from circulation only the infected RBCs, i.e., the direct cause of the malaria pathogenesis. Virtually all other blood components are not affected because separated and purified blood is returned to the patient.

The present invention also differs significantly from current state-of-the-art biocells and magnetic separators in several respects. First, this invention represents a fully integrated system: It draws blood, magnetically separates the pRBCs and the hemozoin from all other cell types, subsequently mechanically traps the pRBCs and the hemozoin in a secondary filter, and replaces the blood (and optionally, plasma) and the other cells into the patient's circulatory systems. Second, blood is propelled through the apparatus's chambers by fluid pumps that allow blood extraction at different outlets at various flow rates to accommodate the specific level of the initial parasitemia of the patient. Third, the invention may be operated in continuous mode. Fourth, the invention represents a novel design that specifically takes into consideration the size and magnetic susceptibility of the pRBC, and allows a high throughput in a compact size. Fifth, the invention collects the pRBCs through one or more outlet portals into one or more collection chambers separated from the separation chambers. This eliminates the issue of the separator clogging under larger levels of parasitemia. Sixth, the invention utilizes disposable separation chambers, and when present, collection chambers. Seventh, the invention requires only small magnetic fields that are achievable with traditional permanent magnets, such as SmCo and NeFeB magnets.

The present invention addresses four significant objectives, each representing a significant advantage over the currently available state-of-the art anti-malarial treatments. First, the invention provides an effective treatment across different malaria endemic regions, despite the heterogeneity of the patient, mosquito, and parasite populations. Consequently, the efficacy of the treatment is not impacted by the parasite's ability to mutate—a significant limitation of the current drugs that are available. The invention has these unique properties because the parasite's magnetic properties, unlike the biological properties, are a direct consequence of all strains of parasites feeding off the RBCs' hemoglobin during the erythrocyte lifecycle. Second, the invention provides a safer treatment with faster recovery and higher cure rate than is currently achievable: i) by rapidly lowering the number of pRBCs and thus improving the blood rheology, and ii) by rapidly reducing the antigen load and the parasite-derived toxins, such as the hemozoin, and thus reducing the metabolic reaction of the immune system. The invention eliminates the immunological risk and high cost associated with the ET process since it significantly reduces and may completely eliminate the need of blood donors (blood transfusion would be needed for only the most severe cases of malaria induced anemia). Third, the invention is applicable also to the most severe cases of malaria, particularly in those patients that may have less than 24 hours before death occurs because of high levels of parasitemia. In these cases, drugs are mostly ineffective in saving life since they require several days to reduce the parasitemia to a non-life threatening threshold. These life threatening events commonly occur in communities with low rates of malaria infection, that because the risk of the disease is low, the initial infection often goes unrecognized and quickly progresses to the stage where drugs are mostly ineffective (These areas include the U.S., West Europe, and India). Finally, the invention significantly reduces the gametocytes present in the blood of the treated patient. By doing so, the invention effectively removes the patient from the transmission cycle. The transmission of the parasite from human to mosquito occurs with the mosquito ingesting gametocytes during a blood meal. Current drugs target the trophozoite form of the parasite and are weakly effective against the gametocyte form. Thus, gametocytes are found in the patient's blood for an extended period of time, as long as two weeks, even after patients are cured from the pathogenicity of the disease. From an epidemic prospective, although these patients are free from the pathogen of the disease, they are still participating in the disease transmission—a serious concern in those endemic regions where large fractions of the population are affected by malaria.

Because this invention eliminates the need of blood donors, it eliminates the cost of blood storage, the cost of screening the transfused blood, and the risk of transmitting infectious diseases from donors to patients and inducing immunological disorders. Furthermore, the process is expected to be particularly-useful in those regions of the world where donors' blood is not readily available. Thus, with respect to the ET treatment the present invention presents a significant lower cost and lower risk. With respect to the anti-malarial drugs, the invention presents a faster, more effective, and universal treatment with fewer side effects, across different species and strains of the *P. falciparum* parasite. It also presents a fast and effective end-stage treatment, and a process to reduce the epidemic and transmission rates.

DESCRIPTION OF THE DRAWINGS

FIG. 2 also shows the line paths that blood and red blood cells take as they flow through the apparatus.

DESCRIPTION OF THE PRESENTLY PREFERRED EMBODIMENTS

Figure 1:
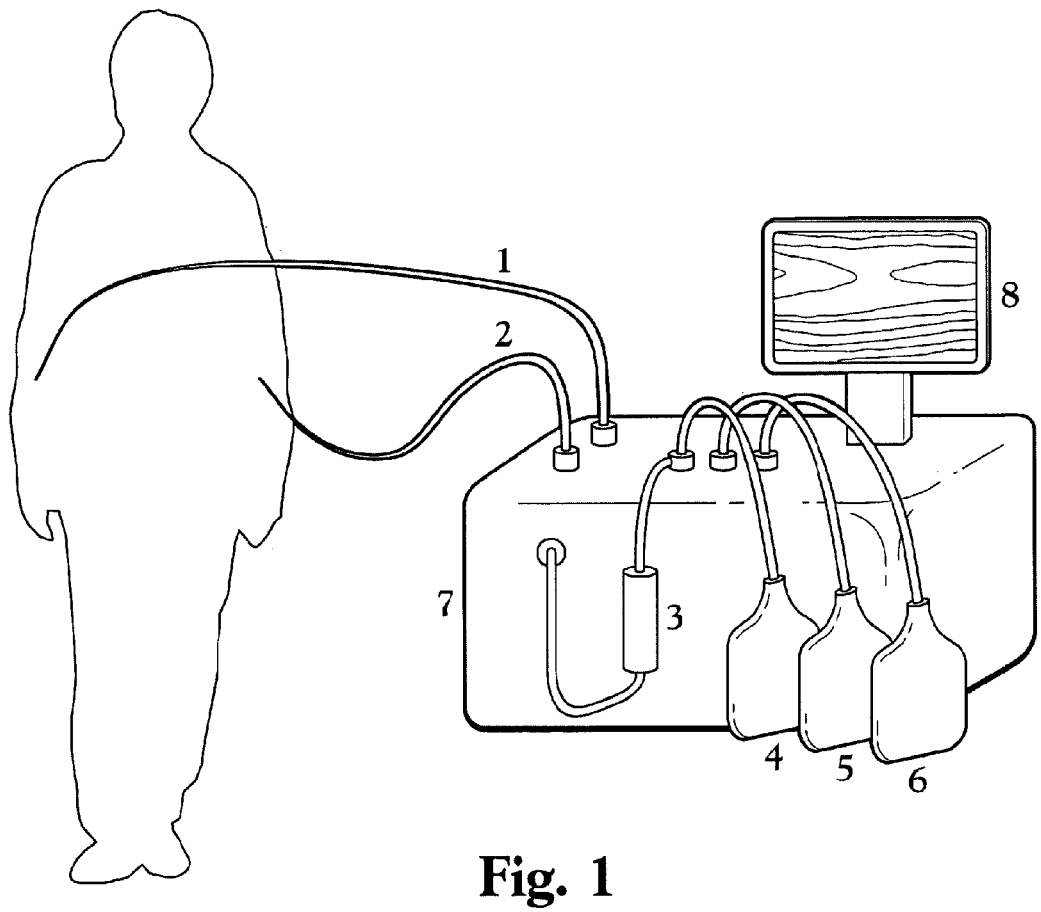
FIG. 1 is a schematic description of the intended use of the present apparatus.

Blood as shown in FIG. 1 is extracted from a malaria-infected patient by means of a set of catheter and tubing and is transferred to the proposed apparatus 7 through a catheter and tubing 1. The apparatus removes the pRBCs and the hemozoin from the patient's blood and returns the cleansed blood to the patient through a second set of catheter and tubing 2. FIG. 1 shows the apparatus membrane filter 3 (also shown as 9 in FIG. 2), and three disposable containers 4, 5 and 6. One of the containers provides intravenous fluid, the second one provides blood-thinning compounds, and the third contains donor blood, which may be optionally be used in some embodiments in order to overcome a high level of anemia. Although the apparatus is designed to eliminate the use of donor blood, in some cases of severe malaria, where anemia is particularly high, patients may need additional donor blood to reduce the risk of anemia induced complication.

The present apparatus is designed to use limited electrical power; pRBC separation may be achieved by permanent magnets, which consume no power, and blood flow may be promoted by low-power pumps. This significantly distinguishes this apparatus from prior art apheresis devices which, by relying on centrifugal forces for cellular separation, uses electrical motors requiring over 1000 watts of electrical power to operate. Because the present invention does not require significant amounts of power, the present apparatus may be powered by a solar panel 8 mounted on the apparatus itself. This feature makes this apparatus a highly versatile and portable blood purification device that may be operated without external power sources.

Figure 2:
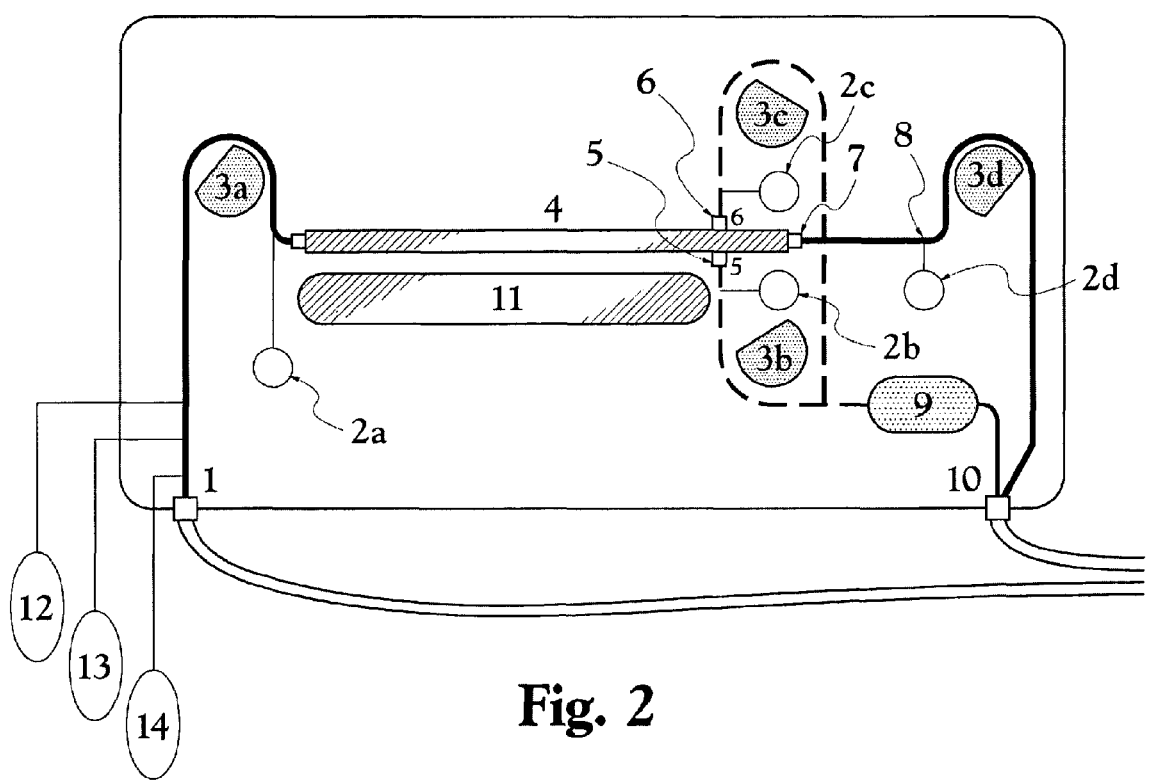
FIG. 2 is a schematic diagram of the apparatus, showing the apparatus's components, tubing, permanent magnet, separation chamber, pumps, inlet and outlet.

Blood enters the apparatus, as depicted in FIG. 2, by a feed 1 and exits to return to the patient by an outlet 10. Blood is propelled by a set of pumps 3a, 3b, 3c, and 3d into the separation chamber 4. The separation chamber has three outlets 5, 6 and 7. Blood from outlet 5 and 6 (dotted lines) is carried to a membrane filter 9 where the pRBCs are collected. The desired pore size of the membrane is only limited on the upper side, and should be smaller than the size of the hemozoin crystal, which is 1-3 μm, and of the pRBCs' average size, which is between 2-8 μm. The membrane filter's role is to remove the pRBCs from plasma and retain the pRBCs for later disposal. Plasma passing through the membrane filter is then reconnected with blood in line 8 before being returned to the patient through outlet 10. A single or a set of permanent magnets 11 is placed in close proximity to the separation chamber. In one currently preferred embodiment of the separation chamber (described next), outlets 5 and 6 are used to extract the pRBCs and the free-hemozoin present in the blood; outlet 7 carries out the non-infected RBCs and all other non magnetic blood components, including most of the plasma. Blood pressure is controlled by a set of pumps, 3a, 3b, 3c, and 3d and monitored by a set of pressure gauges 2a, 2b, 2c and 2d. The particular configuration of the pumps allows achievement of different blood pressures at the chamber outlet 5, 6, and 7. This pump configuration represents a significant improvement over existing prior art. In one embodiment, line 1 may be connected to a container 12, which provides intravenous fluid; to a container 13, which provides blood-thinning compounds; and/or to a third container 14 with donor blood, which may be used in an embodiment designed to overcome high level of anemia.

Figure 3:
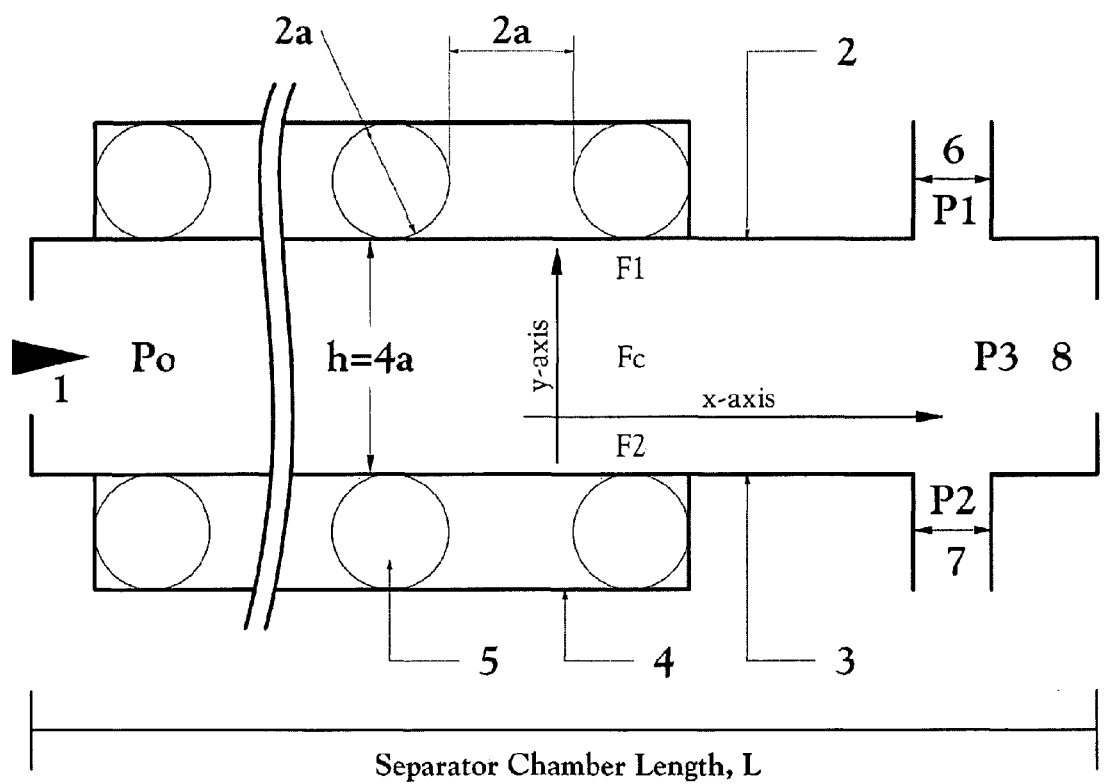
FIG. 3 illustrates the detail of the separation mechanisms.

FIG. 3 illustrates the detail of certain separation mechanisms in a currently preferred embodiment of the present invention. In this figure, the elements of the apparatus are schematized to simplify the description of the separation process. This embodiment is designed to best operate with an input chosen to provide oxygenated blood, for which the RBCs are fully or partially oxygenated, and weakly diamagnetic. As blood enters the separator at 1, it moves in a laminar flow between two plates 2 and 3. The laminar flow is established by creating a pressure gradient along the longitudinal direction of the plates, in this figure represented by the x-axis. Placed above and below the plates are two arrays 4 of iron wires 5 laid uniformly and parallel on the plate and perpendicularly to the x-axis. These wire arrays are referred here as magnetic gradient generators. The chamber ends with three outlets 6, 7, and 8. The pressure P1, P2 and P3 at the three outlets is controlled by the pumps shown in FIG. 3.

A magnetic field is applied using either a single or an array of permanent magnets 11 (FIG. 2), which create a magnetic field ranging between 0.1-1.0 Tesla. The magnetic field has the function to magnetize the wires and the pRBCs. The magnetized wires create a high magnetic gradient.

By properly controlling the blood flow and the size and spacing of the iron wires, and by varying the pressure Po, P1, P2, and P3, cell stratification along the separator cross-section can be controlled and adjusted. While P1, P2 and P3 may differ, this difference may be by only a few PSI. On the other hand, depending on the desired processing rate, the difference between Po and P1, P2 and P3 may be as large as 1 to 10 PSI per cm of chamber length.

The proposed separator offers great flexibility in terms of the critical parameters such as the applied magnetic field and gradient, separator length, and blood flow capacity.

As the pRBCs flow across the chamber, this magnetic field gradient exerts a force on these cells changing their trajectory. Each wire creates an attractive force proportional to $(B^2/a) \times (a/Z)^3$, where a is the radius of the iron wire, B is the magnetic field of several wires created by the permanent magnets, and Z is the distance between the wire and the pRBCs. The pRBCs moving across the separator interacts with several wires, and thus the average impulse that each pRBC experiences is proportional to $(B^2/a) \times (a/Z)^3 \times N$, where N is the average number of wires the pRBCs encounter. By increasing the chamber's length, the number of wires and thus the impulse on the pRBCs can be increased until it is sufficient to displace these cells toward either plate.

As the pRBCs move toward either plates, they also push away all other blood cells that, by being not magnetic are not attracted toward the plates (this includes the non-infected RBCs which in this embodiment have very weak diamagnetism). Thus, as blood flows along the chamber the density of pRBCs begins to increase near the plates' surfaces, while the other blood cells (including the non-infected RBCs) are concentrated at the center of the chamber. At a distance L the segregation of the pRBCs near the plates is completed, after which there will be no more cell arrangement along the y-axis.

As the pRBCs move along the x-axis toward the end of the chamber they reach outlet 5 and 6 (FIG. 2), the pRBCs may experience a decrease in pressure gradient, which is controlled by adjusting the pumps shown in FIG. 2. Under this pressure gradient the pRBCs are deviated from their trajectory along the x-axis and removed from the blood flow. By varying the pressure gradient and the size of the outlets' cross-sections with respect the chamber's cross section, the concentration of removed pRBCs can be controlled. The set of pumps permits dynamic control of the concentration of pRBCs removed as the separation is in process without need to stop the blood flow.

As all other non-magnetic blood cells move toward the end of the chamber they, on the other hand, reach outlet 7 (FIG. 2) where they exit the chamber. Due to similar paramagnetic properties, the free-hemozoin that is present in the blood following the bursting of the pRBCs is expected to follow the same path of the pRBCs, and exit the separation chamber at outlet 5 and 6 where it may be collected in the membrane filter 9 (FIG. 2).

As described above, the magnetic force on pRBCs depends on the wire's radius. As a cell moves away from the wire's surface the force decreases rapidly. Therefore the choice of the wire's radius consequently determines the geometrical dimensions of the whole separation chamber along the vertical axis, which is shown as y-axis in FIG. 3. The chamber size of the present apparatus has been designed to account for this rapid decrease of the magnetic force as the distance between a cell and a wire increases. And for this reason, the chamber's dimensions are expressed in FIG. 3 as a ratio of the wire radius.

Since, at a distance Z of about 2a, the force is decreased by a factor 8, any cells entering the chamber at a distance larger than 2a would effectively experience a reduced force, and thus may move horizontally without a rapid attraction towards the chamber's plates. However, by placing one magnetic field generator at the bottom and one at the top of the chamber, at a distance of about 4a, all cells would experience an equal force for an equal distance from the chamber's walls when entering the chamber, regardless of whether they enter on the bottom or top half of the chamber. Furthermore, the force on the cells would not vary more than about 8 fold along the y-axis. However, if the magnetic field generators were placed too far apart, at a distance larger than 3-4a, it would create a region in the middle of the chamber where the magnetic force is essentially zero. And, thus only the cells entering the chamber in the proximity of the separator surface would be attracted and separated. Finally, if the two magnetic field generators were placed too close to each other, the forces pulling upward and downward would effectively cancel each other out resulting in a overall reduction of the separation efficiency of the apparatus.

The wire's radius affects also the magnitude of the magnetic force. For example, for an iron wire with magnetization of about $½ \times 10^6$ A/m and pRBCs with typical susceptibility of $1\text{-}3 \times 10^{-6}$ in (SI) unit, the magnetic force on a pRBC near the surface of the wire (at the surface the force is maximum) is given by $\sim(6 \times 10^{-5}/a) \times (a/Z)^3$ pN. Blood is a viscous medium, therefore in order to have the pRBCs moving along the y-axis a magnetic force equal or larger than the viscosity force must be applied on the cell. For example, at a velocity of 30 μm/sec a pRBC would typically experience a viscosity force of about 2 pN. By equating the above expression for the magnetic force to the viscosity force of this example, one finds that to achieve separation the radius of these wires should be of the order of 30 μm. This example shows that the magnetic properties of the pRBCs set the size of the wire's radius, which should range between 5-100 μm in the preferred embodiment of the present invention.

The proper length L of the separation chamber, shown in FIG. 3, is related to the radius's wire and the blood flow rate that may be needed. The flow rate itself depends on the pressure difference between point 8 and 1 in FIG. 3. For a typical foreseen application, with blood flowing at a rate of about 6 liter/hours, the apparatus length may range between a few cm to 1-2 meters.

Figure 4:
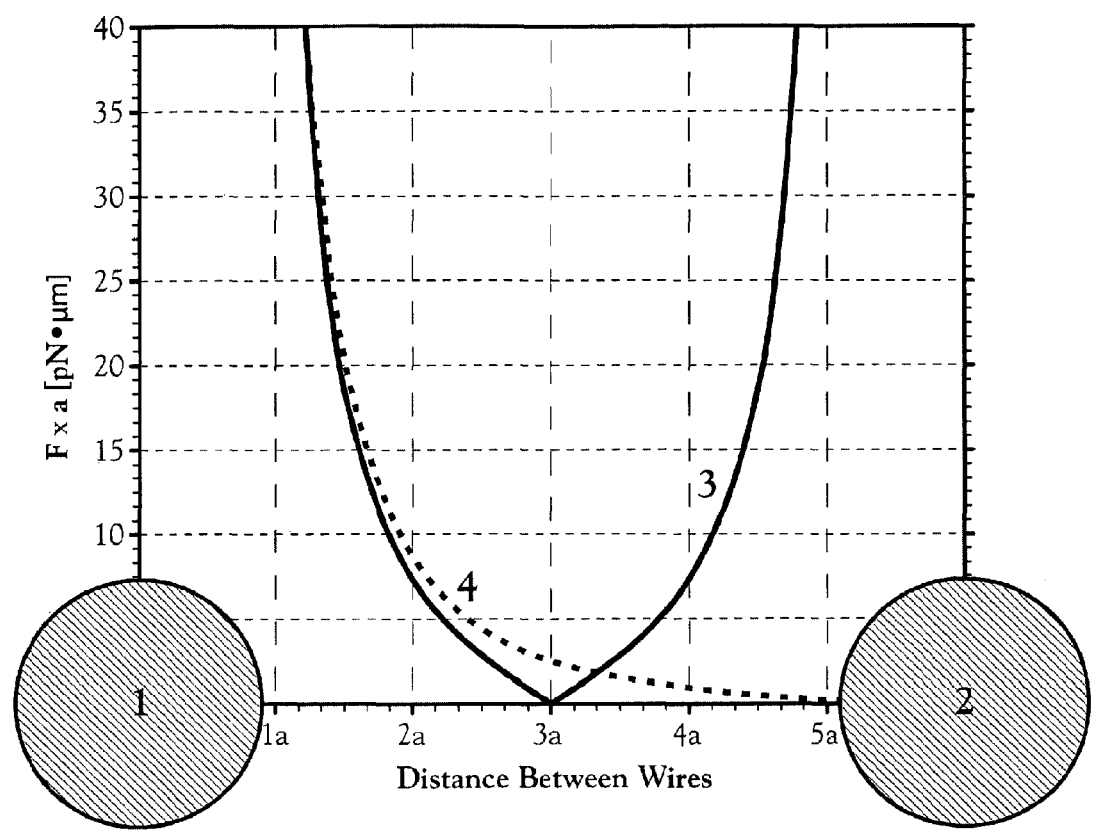
FIG. 4 shows an embodiment in which the magnetic force varies with distance from the separation chamber's bottom along the vertical line between the centers of two wires.

FIG. 4 shows how, in the embodiment of FIG. 3, the magnetic force varies with distance from the chamber's bottom along the vertical line between the centers of two wires. In FIG. 4, the vertical axis represents the product F×a, where "F" is magnetic force on a pRBCs, and "a" is the wires' radius. The product F×a is shown in pN·μm unit. The horizontal axis shows the distance between two wires 1 and 2. The horizontal axis's unit is shown as a multiple of the wires' radius a, e.g., if the wires' radius is 100 μm then the position along the horizontal axis is 200 μm. The solid line 3 shows the magnetic force for an embodiment in which wires are at the top and at the bottom of chamber. The dotted line 4 shows the magnetic force for a currently preferred embodiment with wires position at the bottom of chamber.

Figure 5:
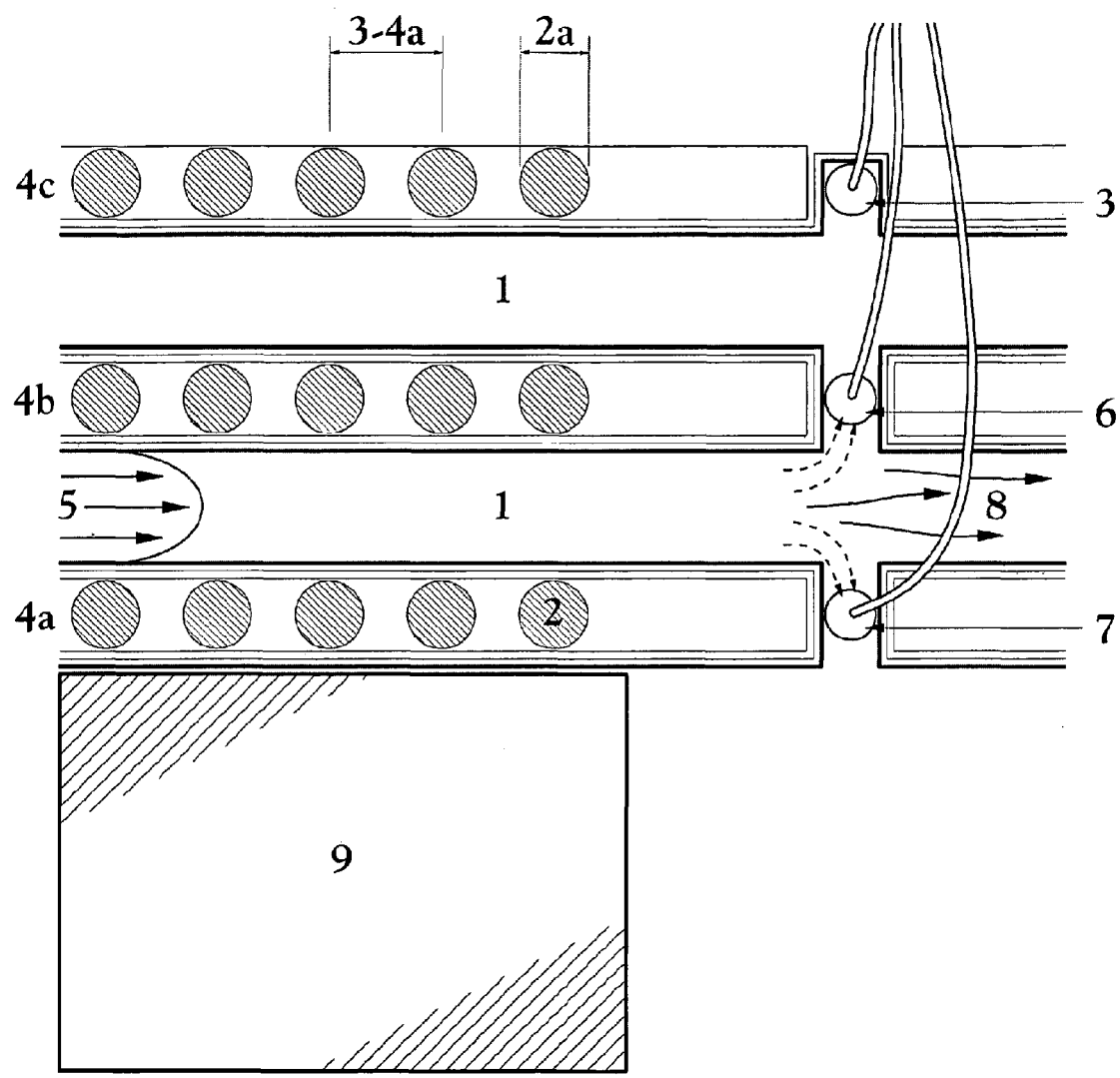
FIG. 5 shows in detail the longitudinal cross section of two elementary units of the separation chamber in one embodiment of the invention.

FIG. 5 shows two elementary units 1 that have been placed in parallel on top of each other. A single magnet or array of magnets 9, placed at the bottom of the lower magnetic gradient generator 4a, are sufficient to magnetize the upper magnetic field generators 4b and 4c. These magnetic gradient generators are composed in this embodiment by an array of wires 2, placed perpendicularly to the chamber longitudinal axis. 6, 7 and 8 show how the blood flows as it reaches the end of the chamber and is separated into the three components previously mentioned. 6 and 7 contain the pRBCs, and 8 contains the non-infected cells. 3 shows the tubing transporting the pRBCs out to the chamber and into the membrane filter.

Figure 6:
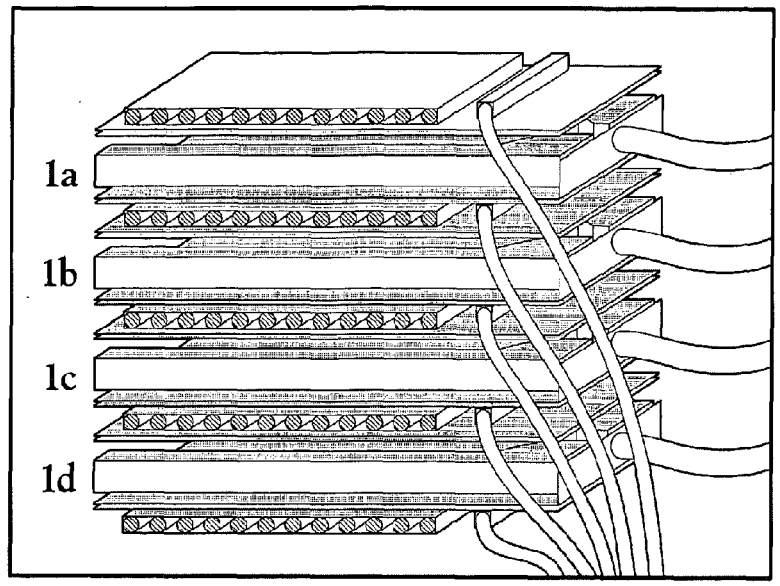
FIG. 6 shows one way in which elementary units may be arranged to form a whole separation chamber of the apparatus of the invention.
Figure 6:
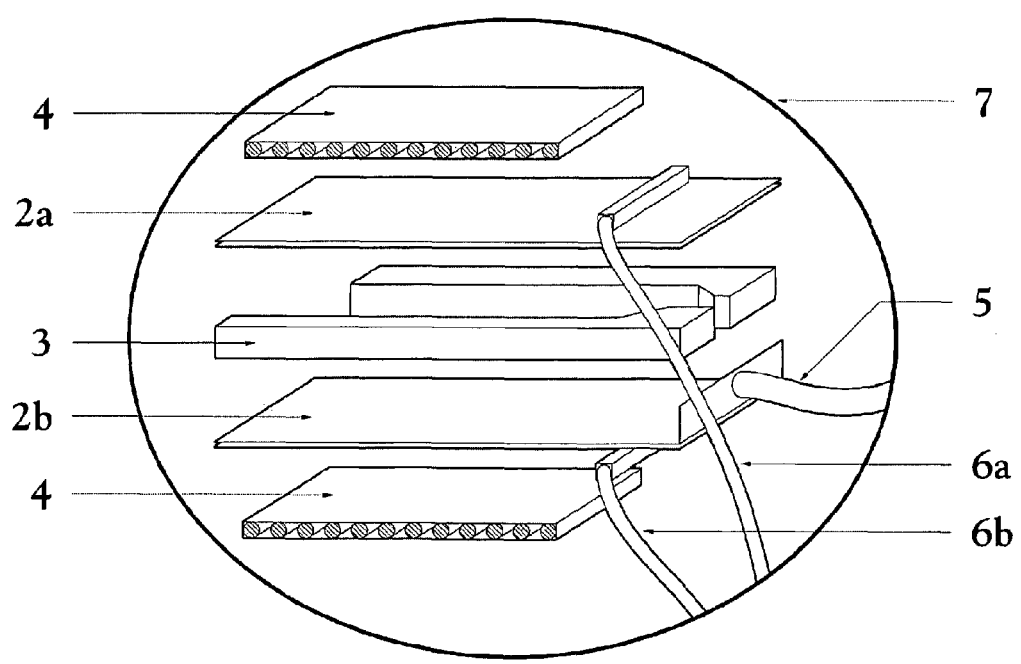

The present apparatus may comprise more than one, e.g., several separation chambers (the elementary units) arranged for example as shown in FIG. 6. In this figure, several separation chambers 1a, 1b, 1c, and 1d, are shown arranged parallel to each other. A magnification 7 of an elementary unit is also shown. These elementary units are composed of a bottom and upper plate 2a and 2b, a chamber wall 3, tubing 5 which is connected to the outlet 8 shown in FIG. 3, and tubing 6b and 6a which are respectively connected to outlets 6 and 7 shown in FIG. 3. Each magnetic gradient generator 4 affects two elementary units, the unit at the top and the unit at the bottom of the magnetic gradient generator. This unique configuration achieves the following goals: i) it allows for a shortening of the device length, while processing the same blood volume per unit of time; ii) it allows for use of smaller permanent magnets and thus reduces cost; iii) the size of the magnetic gradient generator is reduced by a factor of two.

When blood coming into the separation chambers contains fully or partially deoxygenated RBCs, and the RBCs have paramagnetic susceptibility, with respect to the blood plasma, that is larger than the susceptibility of the pRBCs, an embodiment that may be employed is a variation of the embodiment described in FIGS. 3 and 4. In this second embodiment shown in FIG. 6, the upper outlet of the separation chamber is kept close, and the pRBC and the free hemozoin are extracted at outlet 8, and the non-infected RBC from the outlet 6 and 7 shown in FIG. 5.

While certain of the preferred embodiments of the present invention have been described and specifically exemplified above, the invention is in no way intended to be limited to such embodiments. Various modifications may be made to these described embodiments without departing from the scope and spirit of the present invention, as set forth in the following claims.

What is claimed is:

1. A device to enrich non-magnetically responsive blood components, said device comprising:

(a) one or more separation chambers, each one or more separation chambers having one or more entrance ports, one or more exit ports and one or more outlets for directional, continuous movement of blood from the one or more entrance ports through each of the one or more separation chambers and towards the one or more exits ports and one or more outlets, wherein, when subjected to a magnetic field, the non-magnetically responsive blood components flow more readily than magnetically responsive blood components through the one or more exit ports, and the magnetically responsive blood components flow more readily than the non-magnetically responsive blood components through the one or more outlets;

(b) one or more ferromagnetic wires, or one or more wires made of other materials with ferromagnetic or high paramagnetic properties, positioned perpendicular to the longitudinal axis of each of the one or more separation chambers for generating the magnetic field across each of the one or more separation chambers by magnetizing the wires, wherein each of said one or more separation chambers has a width that is at least 100 times larger than the cross-section of the one or more magnetic wires, and wherein said one or more separation chambers are removable from the device; and (c) a plurality of pumps configured to control cell stratification along the separator cross section by varying pressure at the one or more inlet ports, the one or more outlet ports, and the one or more exit ports.

2. The device of claim 1, further comprising a catheter and tubing to remove blood from the patient and propel the blood into the one or more separation chambers by way of the one or more entrance ports.

3. The device of claim 2, wherein the one or more outlets lead to at least one filter which is capable of trapping said magnetically responsive blood components, thereby enriching non-magnetically responsive blood components that flow through the one or more exit ports, wherein the enriched blood components optionally returned to the patient by means of a second catheter and tubing.

4. The device of claim 3, wherein said at least one filter is non-magnetic.

5. The device of claim 1, further comprising a power source for maintaining directional flow of blood from the patient into and out of the one or more separation chambers, wherein the power source is selected from the group consisting of a battery, solar power, geothermal and compressed gas.

6. The device of claim 5, wherein the power source is supplemented by a second power source.

7. The device of claim 1, further comprising a magnet to generate the magnetic field in said wires, wherein the magnet is selected from the group consisting of a permanent magnet, a SmCo magnet, a NeFeB magnet and electromagnetic.

8. The device of claim 7, wherein the magnetic field generated by said magnet ranges from about 0.1 to about 1.0 Tesla.

9. The device of claim 1, wherein a single magnet or a magnet array is used to generate the magnetic field.

10. The device of claim 1, wherein said magnetized wires are made of a magnetic material selected from the group consisting of iron, steel, nickel, cobalt, gadolinium and various magnetic composites.

11. The device of claim 1, wherein one wire array is employed for every two chambers.

12. The device of claim 1, wherein the ratio between the one or more separation chambers' volume and the one one or more wires' volume is $1/5$, and wherein the one or more wires are not in contact with the magnetically responsive blood components and the non-magnetically responsive blood components.

13. The device of claim 7, wherein each of the one or more separation chambers and the magnetic field generator are a single unit that can be removed from the device.

14. The device of claim 1, further comprising one or more pumps, wherein the one or more pumps are removable from the device.

15. The device of claim 14, wherein one or more gauges are incorporated in the device in order to monitor the pressures generated by the one or more of the pumps.

16. The device of 1, wherein width of the outlet is uniform or graded and is between $1/10$ and 4 times the magnetized wire's radius.

17. The device of claim 1, wherein the one or more outlets are removable and replaceable.

18. The device of claim 1, further comprising a membrane filter having a pore size smaller than about 8 μm, said membrane filter being removable and replaceable.

19. A kit comprising one or more separation chambers which is adapted for use with the device according to claim 1.

* * * * *